United States Patent [19]

Winter-Moore et al.

[11] Patent Number: 4,515,565
[45] Date of Patent: May 7, 1985

[54] DENTISTRY

[76] Inventors: Peter H. Winter-Moore, 43 Dunton Hall Rd., Shirley, Solihull B90 2RA, England; Fernando J. Sanchez, 52 Wellington Rd., Edgbaston, Birmingham B15 2ER, England

[21] Appl. No.: 477,766

[22] Filed: Mar. 22, 1983

[30] Foreign Application Priority Data

Mar. 24, 1982 [GB] United Kingdom ............... 8208575
Feb. 4, 1983 [GB] United Kingdom ............... 8303200

[51] Int. Cl.$^3$ .............................................. A61C 5/08
[52] U.S. Cl. ................................................. 433/221
[58] Field of Search .................... 433/221, 220, 225

[56] References Cited

U.S. PATENT DOCUMENTS 4,348,183 9/1982 Weissman ..................... 433/221

FOREIGN PATENT DOCUMENTS 931255 7/1955 France .......................... 433/221

Primary Examiner—Robert Peshock
Attorney, Agent, or Firm—C. O. Marshall, Jr.

[57] ABSTRACT

Figure 2:
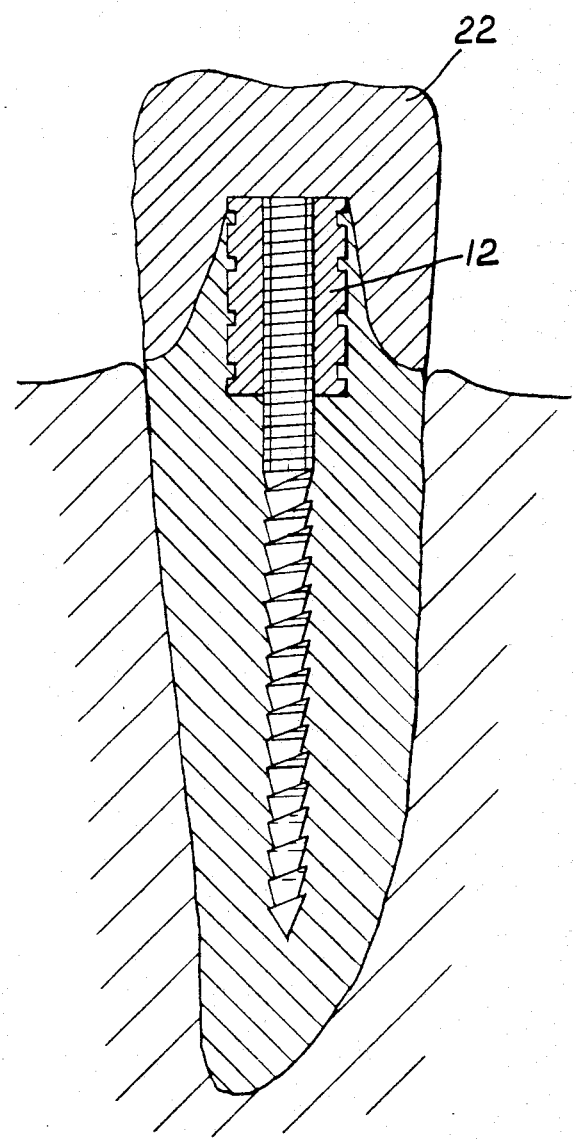

A dental post assembly is for use in crown restoration of anterior teeth and includes a portion intended to screw-tap and engage in the root canal of the tooth and a bush screwthreadedly engaged with the post for insertion into a counter-bore in the upper end of the tooth to act as a lock nut and secure the post in position. FIG. 2 shows the installed dental post in a crowned tooth.

4 Claims, 2 Drawing Figures

DENTISTRY

This invention relates to dentistry and is particularly concerned with preformed post insertion especially, but not exclusively, for crown restoration of anterior teeth.

A widely used method of preformed post insertion currently in use is based on the post and method disclosed in British Pat. No. 1,092,982 (Kurer) in which a parallel-sided (cylindrical) hole is bored and screw tapped in the tooth root and then a screwthreaded post with an enlarged head is inserted into the bore. Although the Kurer post system has a number of advantages over cast post techniques (e.g. cheaper, better retention and easy impression technique), it does suffer from a number of drawbacks including, for example, the absence of anti-rotational features, the danger of fracture of the root during tapping and the requirement for a parallel-sided post hole.

The object of the present invention is to provide a dental post assembly which possesses the advantages of the Kurer post system whilst avoiding at least some of its drawbacks.

According to the present invention we provide a dental post assembly comprising a post provided with means enabling the post to be anchored in the root canal of a tooth in screwthreaded fashion and a bush screwthreadedly engaged with the post whereby the bush can be adjusted lengthwise of the post by relative rotation therebetween.

Preferably the post is provided with a coarse screwthread (i.e. one with a relatively large pitch) for use in anchoring the post to the tooth and a fine screwthread for engagement with the bush. The two screwthreads may be superimposed over at least part of the length of the post.

Conveniently that portion of the post which is to be inserted into the root canal is preferably tapered and the screwthread for anchorage of the post in the tooth is conveniently formed in the manner of a self-tapping screwthread. Advantageously the anchoring screwthread has a barbed profile such that the trailing face of the screwthread is re-entrant thereby providing greater security against axial pullout. In one convenient embodiment, the configuration of said post portion corresponds to the barbed thread profile of a Hedstrom file although it will be understood that the post is not intended for use in the manner of a Hedstrom file.

In practice, it is envisaged that a range of post sizes will be provided and preferably each post size in the range will conform to a respective one of the ISO standard sizes for the longitudinal sections of root canal instruments. In general, the post will be made so as to conform to the larger ISO standard sizes, typically ISO Nos. 120, 130, and 140.

The bush may be textured on its outer surface, as by knurling or serrating it in order to improve its hold in a counterbore formed at the crown end of the tooth cavity and also aid manipulation by the dentist. In some applications, the bush may be provided with a screwthread on its outer surface over at least part of its length so as to provide an anchorage point for a complementary threaded component such as a denture stud. For example, the bush may be stepped in diameter so to comprise a larger diameter portion for entry in the counterbore in the tooth and a smaller diameter portion provided with the external screwthread for anchorage of components such as denture studs.

The post is desirably made of surgical quality stainless steel and the bush may be made of a machine quality brass (e.g. BS 249).

Hence the method of installation is for the dentist to use conventional root instruments to create a tapering cavity in the tooth root and then counterbore the crown end of that cavity. Depending on the size of the file or reamer last used in the preparation of the cavity, a suitable sized post is selected and installed into the cavity so as to project from the root. Thereafter the bush is screwed along the post so as to engage in the counterbore. The bush therefore acts, in effect, as a locking nut to enhance the axial anchorage of the post and also increase its resistance to rotation substantially.

Once the post and bush assembly has been satisfactorily fitted, following any necessary trimming of the post, the assembly is removed, the canal is washed and dried according to endodontic principles, the threads on the post and bush are coated with a suitable cement which is also spun into the root canal, and the assembly is reinstalled. Installation may be carried out using only finger pressure, i.e. without tools, thus reducing the rise of splitting the tooth. Subsequently the surplus portions of the post and bush are ground away and the crown or other component is cemented or otherwise attached to the bush.

Figure 1:
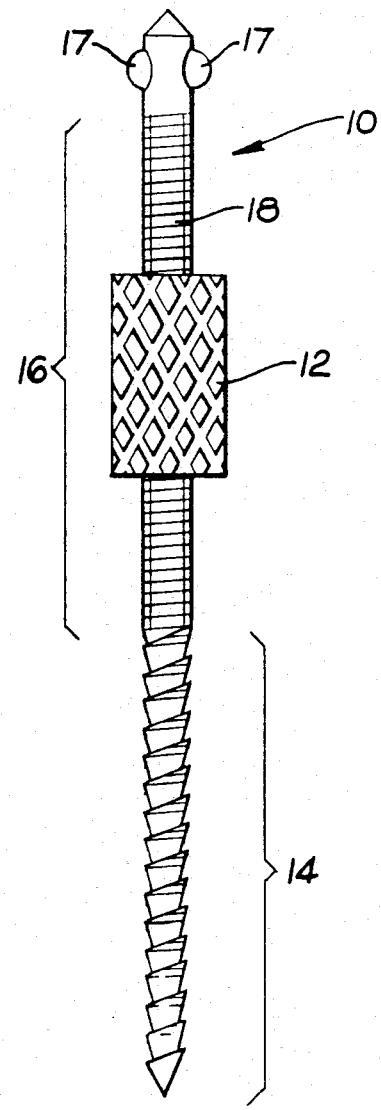

One example of the invention will now be described with reference to the accompanying drawings in which FIG. 1 is a view of a post assembly in accordance with the invention; and FIG. 2 is a view showing the assembly installed in a tooth.

As shown in FIG. 1, the assembly comprises a post 10 and a bush 12. The post comprises a tapering section 14 which may be formed in the manner of a dental file (e.g. a Hedstrom file) having a spiral tooth of barb-like profile, and a generally cylindrical section 16 which may be provided with lateral portions 17 to aid manipulation (and in particular rotation) of the post with the fingers.

The section 16 is provided with a screwthread 18 and the bush 12 is provided with a complementary internal screwthread so that the bush can be adjusted lengthwise along the post by rotation of the bush relative to the post. The screwthread 18 is also superimposed on at least part of the section 14 so that, when circumstances require it, the bush 12 can be adjusted until it at least partly overlaps the section 14.

It is envisaged that a range of post sizes will be manufactured with the respective sections 14 matching ISO Nos. 120, 130 and 140. The length of the post may be a standard size catering for a wide range of possibilities. Where for example a short post is required, the apical portion of the post may be trimmed as necessary.

In use, the root canal of the tooth is prepared in the appropriate manner and will typically be developed to size 110 using hand instruments so far as possible. Unlike the Kurer system, it is not necessary to form a parallel-sided canal since the section 14 of the post is of tapered configuration conforming with ISO sizes. It will be understood that insertion of the post will be effected by rotating it so that the spiral tooth of the tapering section 14 bites into the canal walls in the manner of self-tapping screw and the insertion step can usually be accomplished by handling and manipulating the post within the canal in the same way and using the same sort of forces as routinely used in endodontics. The post size (120, 130 or 140) will be selected according to the binding and length required. After initial insertion, the post is temporarily removed and the apical portion thereof can be trimmed off if required to improve the intimacy of contact with the canal walls and to leave a gap between the post and a previously inserted silver point.

After the post has been found to be a satisfactory fit within the canal, following any trimming that may be necessary, the root face of the tooth is prepared for reception of the bush by means of a root facer to produce a counterbore—see FIG. 2. The post and bush are then fitted to the tooth to ensure a satisfactory fit of the post in the canal and the bush in the counterbore. The bush is intended to be received as a fairly tight fit in the counterbore and for this purpose, it may be knurled or otherwise textured or roughened on its outer surface.

Once a satisfactory fit of post and bush has been obtained, the engaging surfaces of the bush and post and the post and canal walls are coated with a suitable dental cement, the assembly is re-installed and the cement allowed to set to produce secure bonding. It will be noted that the bush acts in the manner of a lock nut and serves to resist both rotation and axial pullout of the post.

After the assembly has been installed, the surplus part of the post is removed and the crown 22 can be fitted after any shaping of the bush that may be considered necessary. In some circumstances, the post assembly may be used for purposes other than crown restoration, e.g. to provide an anchorage for a denture retention stud, and in this instance the bush may be provided with an external screwthread for engagement by a complementary screwthread on the stud. It is even conceivable that the bush itself may be formed integrally with a portion serving as a denture retention stud or the like.

Although the post assembly of the invention is particularly suitable for crown restoration of anterior teeth, and especially narrow rooted teeth such as lower incisors and upper lateral incisors where there is a real danger of perforation or splitting (if the root canals are widened excessively to accommodate a parallel-sided post of the Kurer type), it will be appreciated that the invention is also applicable to posterior teeth and to other dental techniques involving the provision of for example denture stud retainers and coping bars.

Instead of using the post to tap a screwthread into the root canal, a separate tapping tool having a near identical thread may be used for this purpose.

We claim:

1. A dental post assembly comprising a post which
   (a) has its lower end tapered and provided with a barbed self-tapping screwthread having its trailing face reentrant for self-anchoring in an inwardly-tapering hole in a tooth root, and
   (b) has a bush threaded on its upper end for engagement in a counterbore in said hole to serve as a lock nut in cooperation with said self-anchoring screwthread.

2. A post as claimed in claim 1 provided with a coarse screwthread for use in anchoring the post to the tooth and a fine screwthread for engagement with the bush.

3. A post as claimed in claim 2 wherein the two screwthreads are superimposed over at least part of the length of the post.

4. A post as claimed in claim 1 wherein the bush is textured on its outer surface.

* * * * *